US010357339B2

(12) United States Patent
Wang

(10) Patent No.: US 10,357,339 B2
(45) Date of Patent: Jul. 23, 2019

(54) SAFETY SUBANTRAL MEMBRANE LIFT CAPABLE OF DIRECTLY ADJUSTING A SUBANTRAL MEMBRANE TO SAFELY LIFT THE SUBANTRAL MEMBRANE IN A DESIRED DIRECTION BY A DESIRED DISTANCE, AND OPERATING METHOD USING SAME

(75) Inventor: Je-Won Wang, Yuseong-gu (KR)

(73) Assignee: INNOBIOSURG, Daejeon (KR)

( * ) Notice: Subject to any disclaimer, the term of this patent is extended or adjusted under 35 U.S.C. 154(b) by 0 days.

(21) Appl. No.: 14/006,521

(22) PCT Filed: Mar. 21, 2012

(86) PCT No.: PCT/KR2012/002012
§ 371 (c)(1),
(2), (4) Date: Oct. 31, 2013

(87) PCT Pub. No.: WO2012/134094
PCT Pub. Date: Oct. 4, 2012

(65) Prior Publication Data
US 2014/0057228 A1    Feb. 27, 2014

(30) Foreign Application Priority Data
Mar. 25, 2011    (KR) .................. 10-2011-0027180

(51) Int. Cl.
*A61C 8/00*         (2006.01)
*A61B 17/16*        (2006.01)

(52) U.S. Cl.
CPC .......... *A61C 8/0092* (2013.01); *A61C 8/0089* (2013.01); *A61B 17/1673* (2013.01)

(58) Field of Classification Search
CPC ....... A61C 8/0089; A61C 8/0092; A61C 8/00; A61C 8/0018; A61C 8/0022; A61C 8/0039; A61B 17/1673
(Continued)

(56) References Cited

U.S. PATENT DOCUMENTS 5,711,315 A * 1/1998 Jerusalmy ...................... 128/898
6,659,769 B2 * 12/2003 Flanagan ........... A61B 17/1673
                                                         433/144
(Continued)

FOREIGN PATENT DOCUMENTS

EP      1174094 A1 *   1/2002
JP      2007-215912 A  8/2007
(Continued)

OTHER PUBLICATIONS

Communication dated Dec. 14, 2018, issued by Indian Intellectual Property Office in counterpart Indian Patent Application No. 3018/KOLNP/2013.

*Primary Examiner* — Heidi M Eide
*Assistant Examiner* — Mirayda A Aponte
(74) *Attorney, Agent, or Firm* — Sughrue Mion, PLLC

(57) ABSTRACT

Disclosed is a safety subantral membrane lifter including a bone-fixing unit including a bone-fixing arm mounted on the top of the bone-fixing unit, a bone-fixing unit body arranged at the lower end of the bone-fixing unit, and a bone-fixing unit support arranged at the lower end of the bone-fixing unit body. The bone-fixing unit includes a bone-fixing unit body; a bone-fixing arm arranged at one end of the bone-fixing unit body and which is inclined toward one end thereof, two side blades protruding outwardly from both sides of the bone-fixing unit body and formed in the vertical direction so as to be sharp, and a bone-fixing support arranged at the lower end of the bone-fixing unit.

3 Claims, 7 Drawing Sheets

(58) Field of Classification Search
USPC .............................. 433/173, 167, 215, 114
See application file for complete search history.

(56) References Cited

U.S. PATENT DOCUMENTS

| | | | | |
|---|---|---|---|---|
| 7,125,253 | B2* | 10/2006 | Kitamura et al. | 433/173 |
| 7,364,430 | B2* | 4/2008 | Kitamura et al. | 433/173 |
| 7,497,861 | B2* | 3/2009 | Bharadwaj | A61B 17/1635 606/79 |
| 7,510,397 | B2* | 3/2009 | Hochman | 433/172 |
| 7,632,280 | B2* | 12/2009 | Hochman | 606/94 |
| 8,002,548 | B2* | 8/2011 | Lee | 433/173 |
| 8,226,409 | B1* | 7/2012 | Karapetyan | 433/173 |
| 2006/0292523 | A1* | 12/2006 | Elian | 433/173 |
| 2008/0293010 | A1 | 11/2008 | Song | |
| 2008/0319466 | A1 | 12/2008 | Eder | |
| 2010/0081112 | A1* | 4/2010 | Better et al. | 433/174 |
| 2010/0196849 | A1* | 8/2010 | Moneim | A61C 8/0089 433/144 |
| 2010/0221681 | A1* | 9/2010 | Hochman | A61C 8/0033 433/173 |
| 2012/0094254 | A1* | 4/2012 | Uchitel et al. | 433/173 |

FOREIGN PATENT DOCUMENTS

| | | |
|---|---|---|
| KR | 20-0436934 Y1 | 10/2007 |
| KR | 10-2009-0043364 A1 | 5/2009 |

* cited by examiner (1A)   (1B)

(2A)

(2B)            (2C)

(3A)

(3B)

(3C)

(3D)

(3E)

(3F)

(4A)

(4B)

(5A)

(5B)

(6A)

(6B)

(7A)

(7B)

(7C)

SAFETY SUBANTRAL MEMBRANE LIFT CAPABLE OF DIRECTLY ADJUSTING A SUBANTRAL MEMBRANE TO SAFELY LIFT THE SUBANTRAL MEMBRANE IN A DESIRED DIRECTION BY A DESIRED DISTANCE, AND OPERATING METHOD USING SAME

CROSS REFERENCE TO RELATED APPLICATIONS

This application is a National Stage of International Application No. PCT/KR2012/002012 filed Mar. 21, 2012, claiming priority based on Korean Patent Application No. 10-2011-0027180 filed Mar. 25, 2011, the content of all of which are incorporated herein by reference in their entirety.

TECHNICAL FIELD

The present invention relates to a safety subantral membrane lifter comprising a bone-fixing unit including a bone-fixing arm mounted on the top of the bone-fixing unit, a bone-fixing unit body arranged at the lower end of the bone-fixing unit, and a bone-fixing unit support arranged at the lower end of the bone-fixing unit body.

BACKGROUND ART

In early and mid-1990s, implant operation was a very special and scarce clinical area to practicing dentists. In 2000s, the implant industry made a rapid progress in Korea in an industrial and clinical sense for about 10 years, and thus now implant operation is not a special operation any more, and most of dentists are performing implant operation. However, there are still some specific areas of the implant operation, where many dentists are not satisfied, and one of them is implanting maxillary sinus bone.

Maxillary sinus bone implant operation was started in 1960s, and many methods and tools have been developed, but there are still many limitations depending on the proficiency of the dentist and the state of the patient, which have become a stumbling stone to popularization of implant operation.

The subantral membrane is connected with the respiratory organs (nose) to adjust moisture within the nasal cavity, and controls resonance when speaking. When performing implant operation to a patient whose thickness of subantral alveolar bone is thin, the scheme of implant operation may be divided into a lateral approach scheme and a crestal approach scheme.

The lateral approach scheme has good approachability and visibility of the tool, and thus has an advantage capable of separation while controlling the sinus membrane, but because the operated region is wide, the patient's injury increases, various complications (much bleeding, severe adema, acute maxillary sinus inflammation, etc.) may occur.

Further, bone grafting materials may need to be excessively used, and an economic burden may increase due to the needs of materials such as blocking membranes. Further, the biggest problems may be the extension of the operation time and the need of proficiency of the dentist (realistically, only some dentists are able to perform the operation well).

The crestal approach scheme has an advantage that the operated region is small and the operation is simple, but it requires the complicated tool use, and is a completely blind scheme. Further, the approachability of the tool is low, and thus the sinus membrane cannot be directly controlled, thereby increasing the possibility of rupture by concentration of the force. Further, the regulation of the grafting materials is difficult, and thus the self-rupture by the excessive swelling of the sinus membrane may occur, and the bone grafting materials are inserted into a portion which is not the fixture placement portion.

According to a conventional art, when performing implant operation to a patient having a thin subantral alveolar bone, the gum may be opened and the subantral alveolar bone is opened by drilling. Then artificial bone of a certain thickness is grafted to form a desired thickness, and then the implant may be implanted, which is inconvenient. Hence, recently, a complicated operation has been performed to preserve the subantral membrane and the subantral low-cortex alveolar bone as much as possible at the implant operation. However, this method also requires time for fixing the artificial bone and the patient's pain lasts for a long time, and thus there may be many studies to resolve this problem.

For example, Korean patent Publication No. 1020100031273 discloses a maxillary sinus and bone picker which includes an axis 1 including a connection groove 10 at one side, and a cylindrical body (bone picker) 20 including a space therein, wherein the body 20 includes a plurality of cooling water incoming groove 21 which are vertically formed at the side of the edge, a damaged bone removing blade 22 which is spirally projected at one middle end of the side of the body 20, and a cutting unit 23 which is coated by diamond power of micrometer diameter on the lower border.

Korean patent Publication No. 100660375 discloses an implant drill mounted on a dental general hand piece, in which a cutting groove is formed at the outer circumference of the cylindrical body, and a central axis is provided. Further, the implant drill is mounted to be free from the rotation of the drill at the drill end of the body.

Korean patent Publication No. 100838942 discloses a drill including a contact surface having a curved edge which contacts the inner membrane of the maxillary sinus, and a bone-maintaining space for storing and discharging bone grafts. Here, the bone-maintaining space is formed by the connection of the first inner sidewall with the second inner sidewall facing the first inner sidewall, and the first inner sidewall further includes a cutting surface which is exposed in a cutting direction as the first inner sidewall is formed higher than the second inner sidewall.

Korean patent Publication No. 10094573 discloses a subantral membrane bone grafting assembly for artificial bone at the subantral membrane. The subantral membrane bone grafting assembly includes an external drum which is inserted into a hole (H) of an alveolar bone 20, a first internal drum 50 which is inserted into a hollow part 40 of the external drum is formed to contain artificial bone in a depressed portion 51 formed at one end, a cap 70 having a cap magnetic force unit 73 which has the polarity opposite to that of the internal drum magnetic force unit 53 of the first internal drum 50, an external drum driver 60 which is connected to the external drum and inserts the external drum 40 into the alveolar bone, and a second internal drum 80 which is connected to the external drum, is inserted into the hollow part of the external drum, and lifts the subantral membrane.

Korean patent Publication No. 1020100110001 discloses a bone tissue reamer including a tool body 22 which is formed in a manner that the diameter gradually increases from the outer circumference of the upper end to the outer circumference of the lower end, a head 24 which is formed at the upper part of the tool body 22 and has a round (R)

shape for preventing the damage of the subantral membrane at the time of contact with the subantral membrane 30 to life the maxillary sinus, and a water supply hole 28 which is formed at intervals of 120° at the outer circumference of the upper part of the tool body 22, and penetrates a support pole 40, which is formed at the lower part of the tool body 22, and the tool body 22, in which the end of the water supply hole is diverted into three directions.

Korean patent Publication No. 200442905 discloses a drilling device for removing bone capable of protecting soft tissue used when drilling an alveolar bone. The drilling device includes a shank unit which is inserted into the drilling device and is fixed, a body unit which is integrally formed with the shank unit and has a space therein, and an end unit which includes a fixing plate formed inside a space within the body unit, a projected drill blade, and a brush.

DISCLOSURE

Technical Problem

The subantral membrane lifter cannot directly adjust the subantral membrane, and thus the subantral membrane cannot be lifted in a desired direction by a desired distance. Generally, it is difficult to lift the subantral membrane by more than 4 to 5 mm, and as shown in FIG. 5, balanced bone grafting around the implant is impossible because the adhesive force between the subantral membrane and the bone is different depending on the region. Such an operation causes implant operation failure and requires excessive bone grafting. In order to overcome such a failure and limitation, an object of the present invention is to certainly perform bone grafting and use appropriate amount of bone. To this end, a central bone region may be set to remain in a form that the tool may be inserted into up to 1 to 0.5 mm, and drilling is performed so that the subantral membrane lifter may be inserted into the round bone grafts. Then the vertical pressure is gradually applied to lift the bone grafts, on which the subantral membrane is attached, in a desired direction by a desired distance to secure appropriate bone grafting space for implanting.

Technical Solution

In order to solve the above problem, the method according to the present invention has both advantages of the crestal approach and the advantage of the lateral approach. Only the necessary amount is lifted by adjusting the sinus membrane of the region for implanting the implant (fixture), and thus the use of grafting materials may be reduced, and the success rate may be increased without break of the sinus membrane. In detail, the present invention provides a safety subantral membrane lifter comprising a bone-fixing unit including a bone-fixing arm mounted on the top of the bone-fixing unit, a bone-fixing unit body arranged at the lower end of the bone-fixing unit, and a bone-fixing unit support arranged at the lower end of the bone-fixing unit body.

Advantageous Effects

According to the present invention, the bone grafts, on which the subantral membrane is attached, may be lifted in a desired direction by a desired distance, and this is because resistance, which is generated at the time of separation of the maxillary sinus from the subantral membrane, is not concentrated at one side, but is distributed to the area surrounding the space for implanting. Hence, break of the subantral membrane does not occur, the existing lifting list (generally 4 to 5 mm) may be overcome, the bone grafting may be completed with the minimum bone grafting around the mounted implant, and the implant failure may be removed.

BEST MODE

Figure 1:
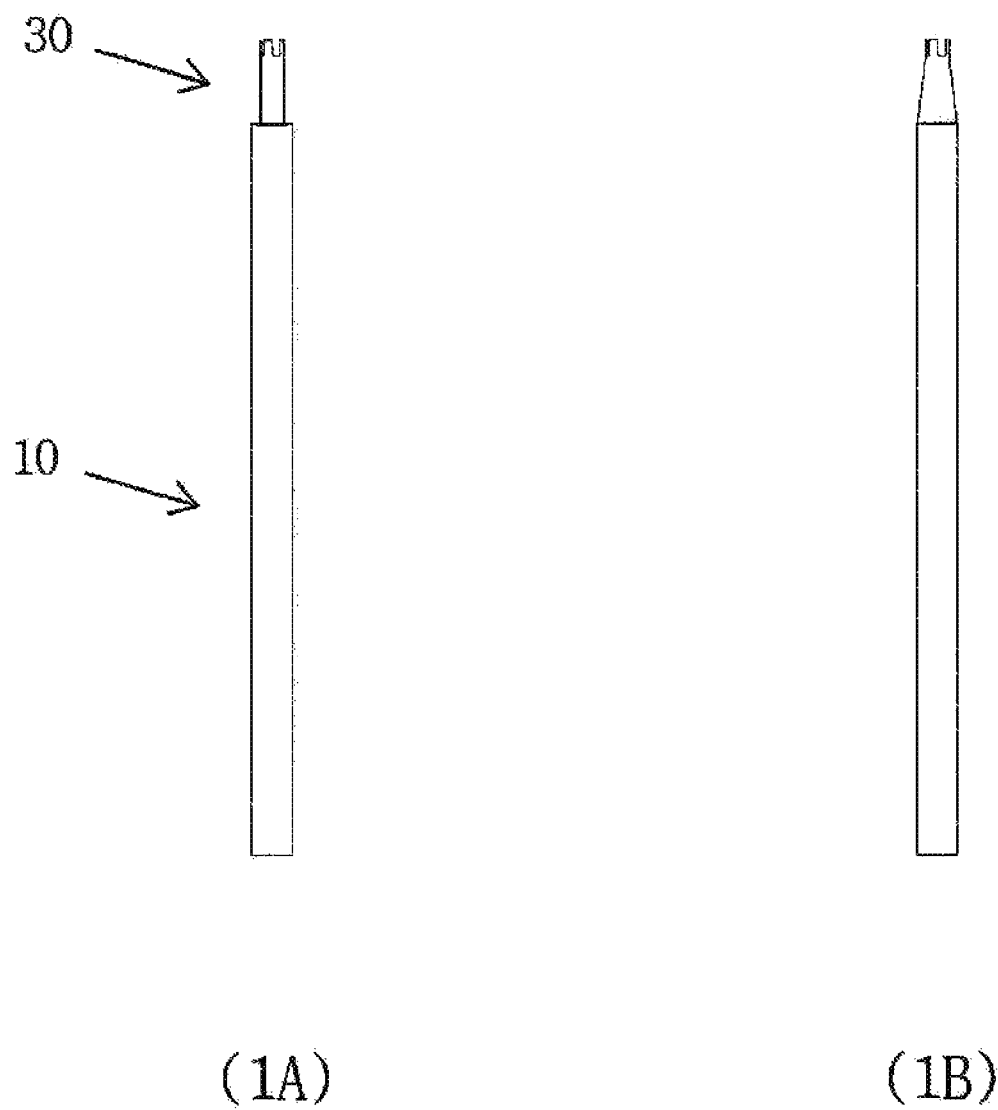
FIG. 1A is a safe subantral membrane lifter capable of directly adjusting a subantral membrane to safely lift the subantral membrane in a desired direction by a desired distance according to an embodiment of the present invention.
FIG. 1B is a safe subantral membrane lifter capable of directly adjusting a subantral membrane to safely lift the subantral membrane in a desired direction by a desired distance according to another embodiment of the present invention.

The gum of the portion for implant is cut, the first drilling is performed by using the first implant drilling tool to form a groove (FIG. 7A), and the bone-fixing unit of the subantral membrane lifter (safety subantral membrane lifter capable of directly adjusting a subantral membrane to safely lift the subantral membrane in a desired direction by a desired distance) is inserted into the groove and the lower end of the support is struck by a hammer to apply force (vertical force). Then the maxillary sinus and the bone are broken, the alveolar bone held by the bone-fixing unit is moved to the upper part so as to push the subantral membrane to the upper part (FIG. 7B), and thus the subantral membrane is directly adjusted so that the subantral membrane may be safely lifted in a desired direction by a desired distance. Then the safety subantral membrane lifter is returned, the alveolar bone and artificial bone at the internal space of the bone-fixing unit 30 are mixed, and the mixture is appropriately pushed into a space between the subantral membrane and the maxillary sinus. Then the implant is placed in the space (FIG. 7C) and the subantral membrane lifter's position is adjusted for implant operation.

DETAILED DESCRIPTION OF EXEMPLARY EMBODIMENTS

The present invention relates to a safety subantral membrane lifter including a bone-fixing unit including a bone-fixing arm mounted on the top of the bone-fixing unit, a bone-fixing unit body arranged at the lower end of the bone-fixing unit, and a bone-fixing unit support arranged at the lower end of the bone-fixing unit body.

The bone-fixing unit includes the bone-fixing unit body, which is cylindrical and which has an open end and a space formed therein, the bone-fixing arm arranged at one end of the bone-fixing unit body and which is inclined toward one end thereof, two side blades protruding outwardly from both sides of the bone-fixing unit body and formed in the vertical direction so as to be sharp, and the bone-fixing support arranged at the lower end of the bone-fixing unit. The safety subantral membrane lifter of the present invention may directly adjust the subantral membrane to safely lift the subantral membrane in a desired direction by a desired distance.

Generally, a maxilla (upper jaw) includes a cortex alveolar bone, a cancellous alveolar bone, a subantral low-cortex alveolar bone, a subantral membrane, and a maxillary antrum, and there is space connected to the nose on the upper part of the subantral membrane.

The subantral membrane is connected with the respiratory organs (nose) to adjust moisture within the nasal cavity, controls resonance when speaking, is elastic, and is not easily injured.

Hence, part of the low cortex alveolar bone is made to be broken by using the device of the present invention, and is moved along with the subantral membrane on which the alveolar bone is attached, and the space part to which the subantral membrane has been moved is filled with the artificial bone, then the implant (fixture) is implanted to minimize the injury of the lifted subantral membrane.

As shown in FIG. 7A, the central part remains in a form such that the tool may be inserted up to 1 to 0.5 mm of the maxillary sinus, and other parts are drilled. Then the subantral membrane lifter is inserted into bone grafts, and vertical pressure is gradually applied in order to lift the bone grafts, on which the subantral membrane has been attached, in a desired direction by a desired distance (this is because resistance, which is generated at the time of separation of the maxillary sinus from the subantral membrane, is not concentrated at one side, but is distributed to the area surrounding the space for implanting).

Hence, break of the subantral membrane does not occur, the existing lifting list (generally 4 to 5 mm) may be overcome, the bone grafting may be completed with the minimum bone grafting around the mounted implant, and the implant failure may be removed.

Hereinafter, the present invention will be described through embodiments.

Exemplary Embodiment

The gum of the portion for implant is cut, the first drilling is performed by using the first implant drilling tool to form a groove (FIG. 7A), and the bone-fixing unit of the subantral membrane lifter (safety subantral membrane lifter capable of directly adjusting a subantral membrane to safely lift the subantral membrane in a desired direction by a desired distance) is inserted into the groove and the lower end of the support is struck by a hammer to apply force (vertical force). Then the maxillary sinus and the bone are broken, the alveolar bone held by the bone-fixing unit is moved to the upper part so as to push the subantral membrane to the upper part (FIG. 7B), and thus the subantral membrane is directly adjusted so that the subantral membrane may be safely lifted in a desired direction by a desired distance. Then the safety subantral membrane lifter is returned, the alveolar bone and artificial bone at the internal space of the bone-fixing unit 30 are mixed, and the mixture is appropriately pushed into a space between the subantral membrane and the maxillary sinus. Then the implant is placed in the space (FIG. 7C) and the subantral membrane lifter's position is adjusted for implant operation.

Hereinafter, the present invention will be described in detail with reference to the attached drawings.

Figure 2:
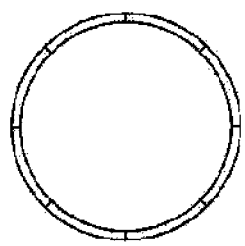
FIG. 2A is an extended view of a bone-fixing unit of the safe subantral membrane lifter shown in FIG. 1A.
FIG. 2B is an extended view of a bone-fixing unit of the safe subantral membrane lifter shown in FIG. 1B.
Figure 2:
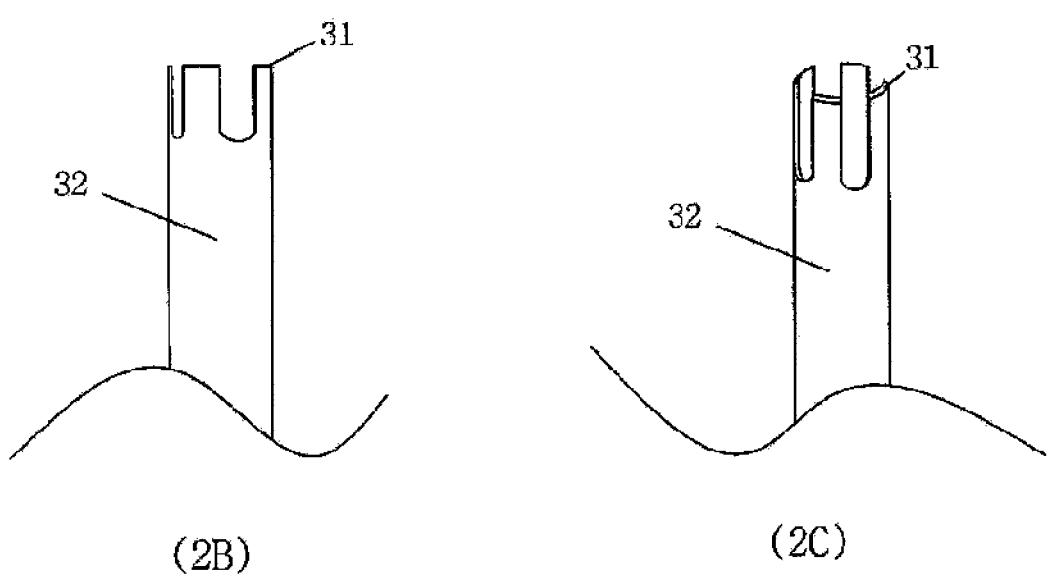
Figure 3:
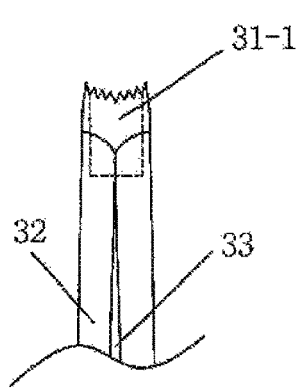
FIG. 3A illustrates an example of a bone-fixing unit of the present invention.
FIG. 3B illustrates another example of a bone-fixing unit of the present invention.
FIG. 3C illustrates yet another example of a bone-fixing unit of the present invention.
FIG. 3D illustrates yet another example of a bone-fixing unit of the present invention.
FIG. 3E illustrates yet another example of a bone-fixing unit of the present invention.
FIG. 3F illustrates yet another example of a bone-fixing unit of the present invention.
Figure 3:
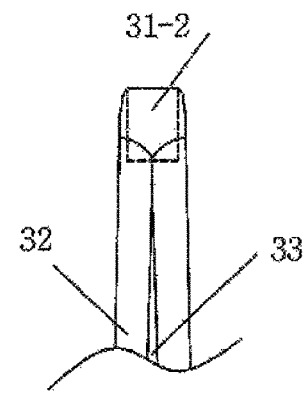
Figure 3:
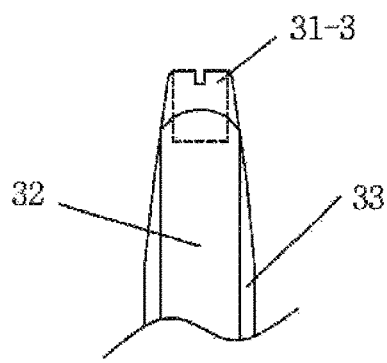
Figure 3:
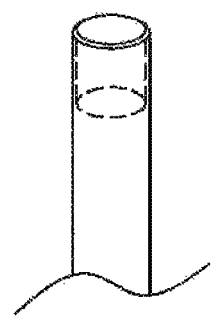
Figure 3:
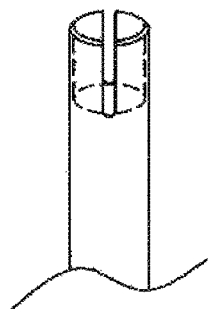
Figure 3:
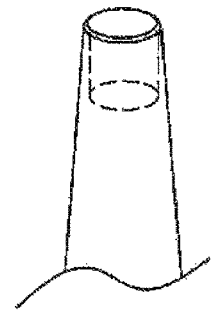
Figure 4:
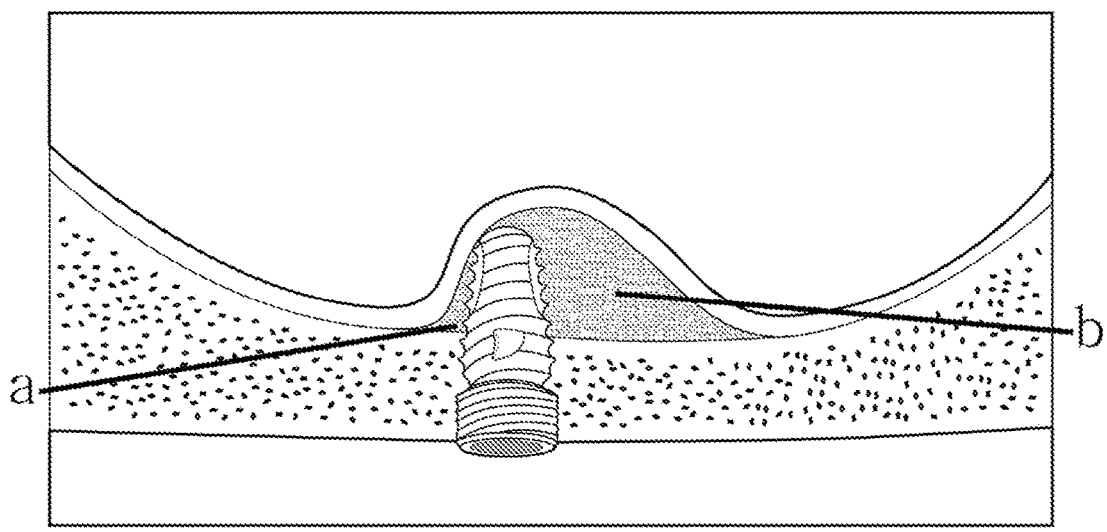
FIG. 4A is a view illustrating a state of lifting a subantral membrane by using a conventional subantral membrane lifter.
FIG. 4B is another view illustrating a state of lifting the subantral membrane by using the conventional subantral membrane lifter.
Figure 4:
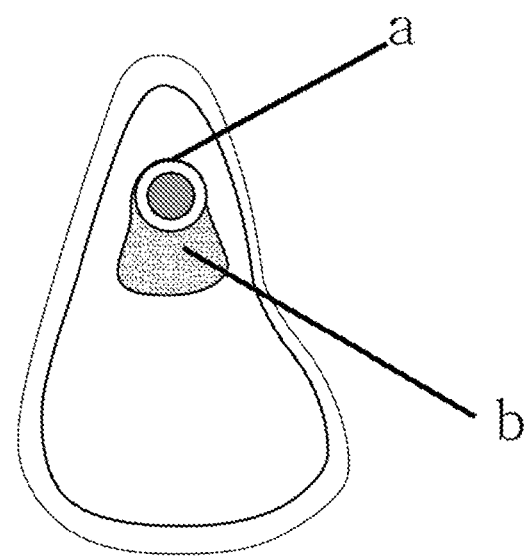
Figure 5:
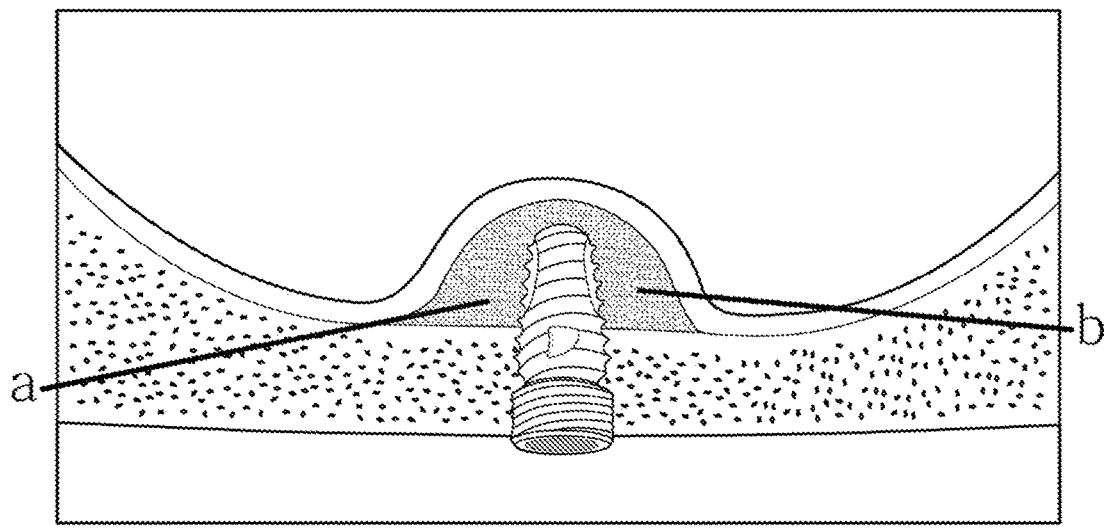
FIG. 5A is a view illustrating a state of lifting a subantral membrane according to an embodiment of the present invention.
FIG. 5B is another view illustrating a state of lifting the subantral membrane according to the embodiment shown in FIG. 5A.
Figure 5:
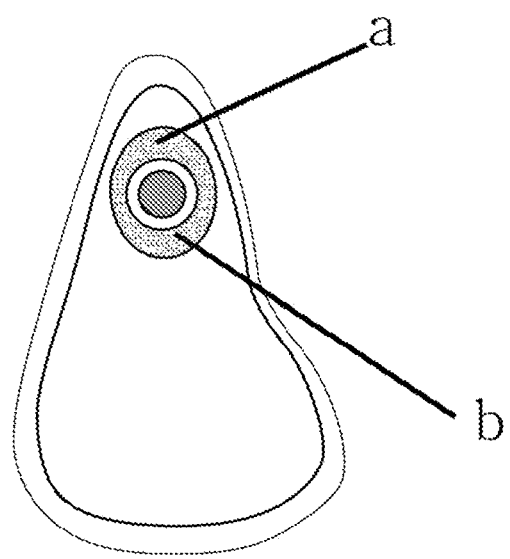
Figure 6:
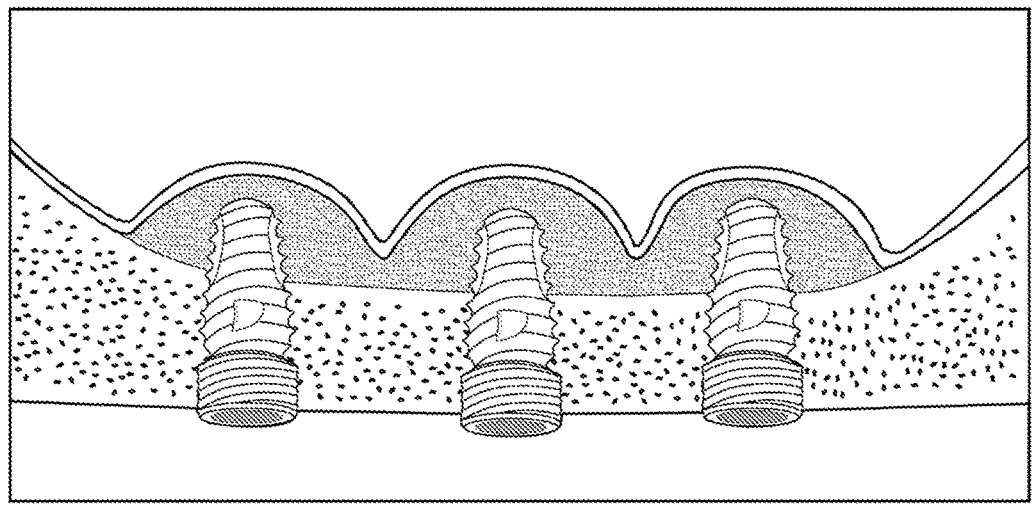
FIG. 6A is a view illustrating a state of lifting a subantral membrane according to another embodiment of the present invention.
FIG. 6B is another view illustrating a state of lifting the subantral membrane according to the embodiment shown in FIG. 6A.
Figure 6:
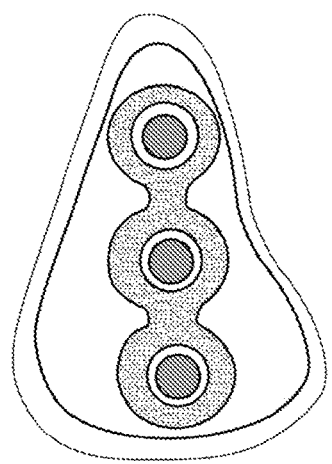
Figure 7:
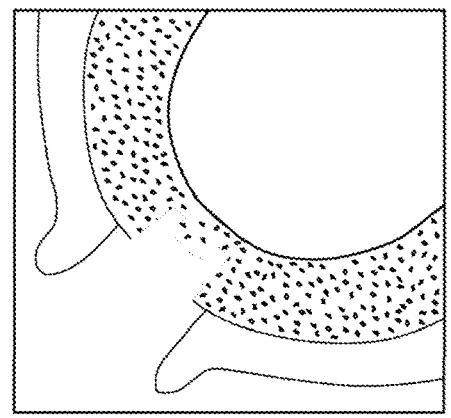
FIG. 7A is a first view of a flowchart illustrating a method of directly adjusting a subantral membrane to safely lift the subantral membrane in a desired direction by a desired distance according to an embodiment of the present invention.
FIG. 7B is a second view of the flowchart illustrating the method of directly adjusting the subantral membrane to safely lift the subantral membrane according to the embodiment of the present invention.
FIG. 7C is a third view of the flowchart illustrating the method of directly adjusting the subantral membrane to safely lift the subantral membrane according to the embodiment of the present invention.
Figure 7:
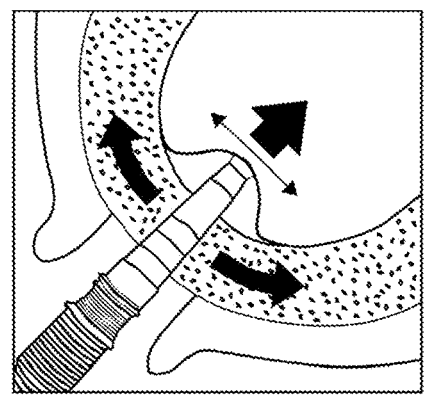
Figure 7:
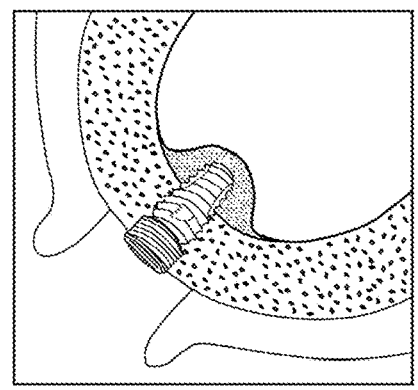

FIG. 1 is a safe subantral membrane lifter capable of directly adjusting a subantral membrane to safely lift the subantral membrane in a desired direction by a desired distance according to an embodiment of the present invention, FIG. 2 specifically illustrates a bone-fixing unit of the present invention, FIG. 3 illustrates another example of a bone-fixing unit of the present invention, FIG. 4 illustrates a state of lifting a subantral membrane by using a conventional subantral membrane lifter, FIGS. 5 and 6 illustrate a state of lifting a subantral membrane according to an embodiment of the present invention, and FIG. 7 is a flowchart illustrating a method of directly adjusting a subantral membrane to safely lift the subantral membrane in a desired direction by a desired distance according to an embodiment of the present invention. The bone-fixing unit 30, the bone-fixing arm 31, the bone-fixing unit body 32, the side blade 33, and the bone-fixing unit support 10 are provided.

The structure will described below.

As illustrated in FIGS. 1 and 2, the safe subantral membrane lifter capable of directly adjusting a subantral membrane to safely lift the subantral membrane in a desired direction by a desired distance includes the following.

Referring to FIG. 1A, the safe subantral membrane lifter includes a bone-fixing unit support 10 and a bone-fixing unit 30 mounted on the top of the bone-fixing unit support 10.

The bone-fixing unit 30 includes a bone-fixing unit body 32 (whose diameter is 1 to 6 mm), which is cylindrical and which has an open end and a space (having a depth of 0.2 mm to 7 mm) formed therein. Further, the end of the bone-fixing unit body 32 includes a bone-fixing arm 31 having a plurality of projects which are spaced at regular intervals.

Referring to FIG. 1B, the safe subantral membrane lifter includes a bone-fixing unit support 10 and a bone-fixing unit 30 mounted on the top of the bone-fixing unit support 10.

The bone-fixing unit 30 includes a bone-fixing unit body 32 (whose diameter is 1 to 6 mm), which is cylindrical and which has an open end and a space (having a depth of 0.2 mm to 7 mm) formed therein.

Further, the end of the bone-fixing unit body 32 includes a bone-fixing arm 31, which is inclined towards the end and has a plurality of projects which are spaced at regular intervals.

FIGS. 2 and 3 show that the bone-fixing arm 31, which forms the end of the bone-fixing unit 30, has various shapes.

FIG. 2A is an extended view of the bone-fixing unit 30 of FIG. 1A, and FIG. 2B is an extended view of the bone-fixing unit 30 of FIG. 1B.

FIG. 3 illustrates another example of the bone-fixing unit of the present invention.

Referring to FIG. 3A, the bone-fixing unit 30 includes a bone-fixing unit body 32 (whose diameter is 1 to 6 mm), which is cylindrical and which has an open end and a space (having a depth of 0.2 mm to 7 mm) formed therein.

The bone-fixing unit 30 further includes a bone-fixing arm 31-1 arranged at one end of the bone-fixing unit body 32 and which is inclined toward one end thereof, and two side blades protruding outwardly from both sides of the bone-fixing unit body 32 and formed in the vertical direction.

Referring to FIG. 3B, the bone-fixing unit 30 includes a bone-fixing unit body 32 (whose diameter is 1 to 6 mm), which is cylindrical and which has an open end and a space (having a depth of 0.2 mm to 7 mm) formed therein.

The bone-fixing unit 30 further includes a bone-fixing arm 31-2 having the same height of the end as that of the bone-fixing unit body 32.

The bone-fixing unit 30 further includes two side blades 33 protruding outwardly from both sides of the bone-fixing unit body 32 and formed in the vertical direction so as to be sharp.

Referring to FIG. 3C, the bone-fixing unit 30 includes a bone-fixing unit body 32 (whose diameter is 1 to 6 mm), which is cylindrical and which has an open end and a space (having a depth of 0.2 mm to 7 mm) formed therein.

The bone-fixing unit 30 further includes two bone-fixing arms 31-3 which are separated on the basis of the central part of the bone-fixing unit body 32.

The bone-fixing unit 30 further includes two side blades 33 protruding outwardly from both sides of the bone-fixing unit body 32 and formed in the vertical direction so as to be sharp.

Referring to FIG. 3D, the bone-fixing unit 30 includes a bone-fixing unit body 32 (whose diameter is 1 to 6 mm), which is cylindrical and which has an open end and a space formed therein, and a bone-fixing arm 31 arranged at one end of the bone-fixing unit body and which is inclined toward one end thereof.

Referring to FIG. 3E, the bone-fixing unit 30 a bone-fixing unit body 32, which is cylindrical and which has an open end and a space formed therein, and bone-fixing arms 31 arranged at one end of the bone-fixing unit body and which are inclined toward one end thereof, and which are separated on the basis of the central part.

Referring to FIG. 3F, the bone-fixing unit 30 includes a bone-fixing unit body 32, which is cylindrical and which has an open end and a space formed therein, and a bone-fixing arm 31 arranged at one end of the bone-fixing unit body and which is inclined toward one end thereof.

FIG. 4 illustrates a state of lifting a subantral membrane by using a conventional subantral membrane lifter. The distribution of the grafted bone of the implant of the left side (a) is different from that of the right side (b), and because the right side (a) having less grafted bone is weak, the implant function failure may occur.

FIGS. 5 and 6 illustrate a state of lifting a subantral membrane by using a safe subantral membrane lifter capable of directly adjusting a subantral membrane to safely lift the subantral membrane in a desired direction by a desired distance according to an embodiment of the present invention, and because the distribution of the grafted bone of the implant is balanced in the left side (a) and the right side (b), the implant function failure does not occur.

A view illustrating a state of use of a safe subantral membrane lifter capable of directly adjusting a subantral membrane to safely lift the subantral membrane in a desired direction by a desired distance according to an embodiment of the present invention will be described below.

Referring to FIG. 7, The gum of the portion for implant is cut, the first drilling is performed by using the first implant drilling tool to form a groove (FIG. 7A), and the bone-fixing unit of the subantral membrane lifter is inserted into the groove and the lower end of the support is struck by a hammer to apply force (vertical force). Then the maxillary sinus and the bone are broken, the alveolar bone held by the bone-fixing unit is moved to the upper part so as to push the subantral membrane to the upper part, and thus the subantral membrane is directly adjusted so that the subantral membrane may be safely lifted in a desired direction by a desired distance. Then the safety subantral membrane lifter is returned, the alveolar bone and artificial bone at the internal space of the bone-fixing unit 30 are mixed, and the mixture is appropriately pushed into a space between the subantral membrane and the maxillary sinus. Then the implant is placed in the space and the subantral membrane lifter's position is adjusted for implant operation.

INDUSTRIAL APPLICABILITY

The bone grafts, on which the subantral membrane is attached, may be lifted in a desired direction by a desired distance, and this is because resistance, which is generated at the time of separation of the maxillary sinus from the subantral membrane, is not concentrated at one side, but is distributed to the area surrounding the space for implanting. Hence, break of the subantral membrane does not occur, the existing lifting list (generally 4 to 5 mm) may be overcome, the bone grafting may be completed with the minimum bone grafting around the mounted implant, and the implant failure may be removed.

The invention claimed is:

1. A safety subantral membrane lifter for safely lifting a subantral membrane in a desired direction by a desired distance by directly adjusting the subantral membrane, the safety subantral membrane lifter comprising:
   a bone-fixing unit support extending in a vertical direction; and
   a bone-fixing unit which is mounted on an upper part of the bone-fixing unit support and extends in the vertical direction,
   wherein a diameter of the bone-fixing unit is 1 to 6mm,
   wherein the bone-fixing unit comprises:

a bone-fixing unit body which is cylindrical and which has an open end and a space formed therein and extends in the vertical direction;

a bone-fixing arm arranged at the open end of the bone-fixing unit body and having an outer surface which is inclined narrowly from the open end of the bone-fixing unit body toward the outer end of the bone-fixing arm; and two side blades, wherein each side blade of the two side blades protrudes outwardly from opposing sides of an outer surface of the bone-fixing unit body in a horizontal direction perpendicular to the vertical direction and each side blade of the two side blades extends in the vertical direction to be sharp, the two side blades protruding outwardly from the opposing sides of the outer surface of the bone-fixing unit body, respectively, wherein a thickness of the each side blade of the two side blades gradually increases from the open end of the bone-fixing unit body toward the upper part of the bone-fixing unit support, wherein when the open end of the safety subantral membrane lifter is inserted into a groove on alveolar bone and the bone-fixing unit body is struck, a broken alveolar bone held by the bone-fixing unit is moved so as to push the subantral membrane.

2. The safety subantral membrane lifter of claim 1, wherein a depth of the space of the bone-fixing unit body is between 0.2 mm and 7 mm.

3. A method of operation by using the safety subantral membrane lifter of claim 1, the method comprising:

cutting a portion of a gum for operation;

forming a groove by performing a first drilling by using a first implant drilling tool;

inserting the bone-fixing unit of the subantral membrane lifter into the groove and striking a lower end of the bone-fixing unit support by using a hammer to apply force to that a maxillary sinus bone is broken, an alveolar bone held by the bone-fixing unit is moved in a first direction so as to push the subantral membrane in the first direction, and thereby the subantral membrane is directly adjusted so that the subantral membrane is safely lifted in a desired direction by a desired distance;

moving the safety subantral membrane lifter in a second direction opposite to the first direction;

mixing the alveolar bone held by the bone-fixing unit and artificial bone to form an amount of a mixture of the alveolar bone and the artificial bone;

pushing the amount of the mixture of the alveolar bone and the artificial bone into a space between the subantral membrane and the maxillary sinus; and adjusting a position of the subantral membrane by placing an implant in the space.

* * * * *